United States Patent [19]

Roncucci et al.

[11] 4,318,706
[45] Mar. 9, 1982

[54] PROCESS FOR DETERMINING MALONDIALDEHYDE

[75] Inventors: Roméo Roncucci, Paris, France; Jacqueline Lansen, Anderlecht, Belgium

[73] Assignee: Continental Pharma, Brussels, Belgium

[21] Appl. No.: 88,726

[22] Filed: Oct. 26, 1979

[30] Foreign Application Priority Data

Oct. 27, 1978 [LU] Luxembourg .......................... 80437

[51] Int. Cl.³ ............................................ G01N 33/52
[52] U.S. Cl. .................................... 23/230 B; 422/81
[58] Field of Search .................. 23/230 B; 422/82, 81

[56] References Cited

U.S. PATENT DOCUMENTS

| 2,797,149 | 6/1957 | Skeggs | 23/230 R |
| 3,804,593 | 4/1974 | Smythe | 422/82 X |
| 3,876,374 | 4/1975 | Burns | 422/82 X |

FOREIGN PATENT DOCUMENTS 2029884  6/1970  Fed. Rep. of Germany .
816023   7/1959  United Kingdom .
986464   3/1965  United Kingdom .

OTHER PUBLICATIONS

Chemical Abstracts, 87:196686s (1977).
Chemical Abstracts, 88:72128n (1978).

*Primary Examiner*—Sidney Marantz
*Attorney, Agent, or Firm*—Sughrue, Mion, Zinn, Macpeak and Seas

[57] ABSTRACT

A process and an apparatus for determining malondialdehyde content of blood platelets.

A platelet-enriched plasma is prepared from a determined amount of blood, the counting of the platelets is carried out, the platelets are sedimented, an aggregation agent is added, segmented samples are prepared, said samples are submitted to a dialysis in order to eliminate the proteins and the malondialdehyde content is determined by colorimetry. The samples are segmented with a gas.

The process is particularly suitable for evaluating the platelet regeneration.

5 Claims, 1 Drawing Figure

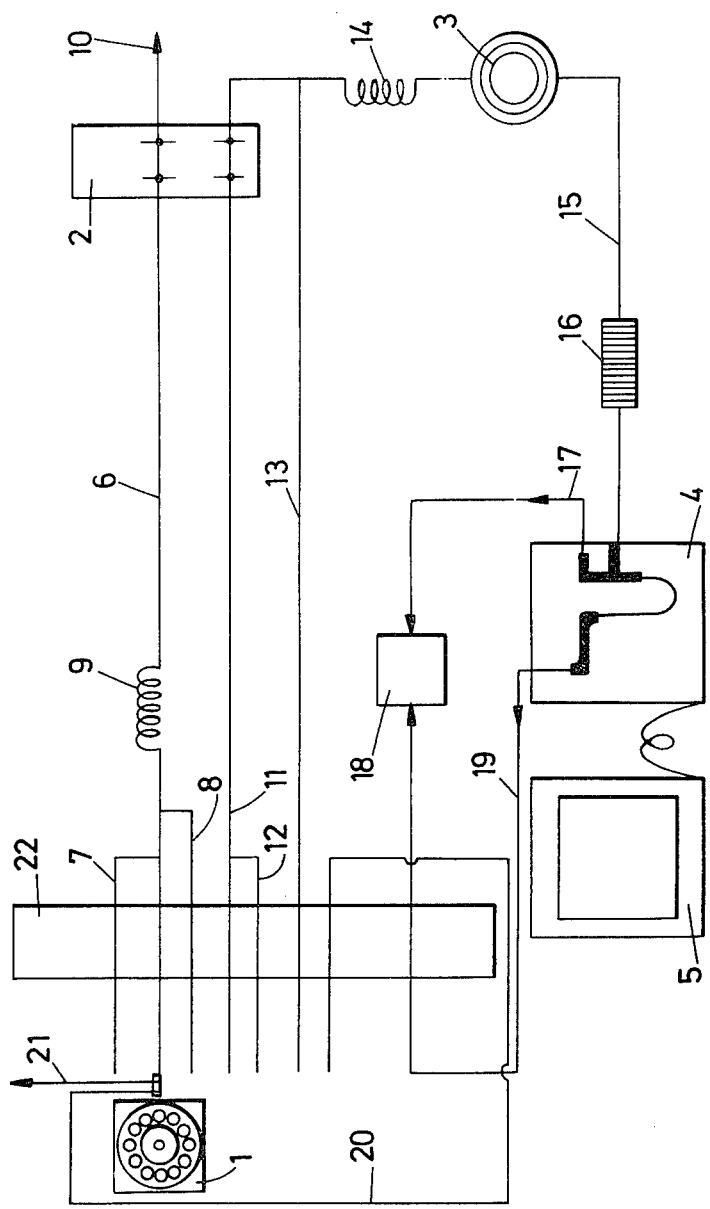

PROCESS FOR DETERMINING MALONDIALDEHYDE

This invention relates to a process for determining the content of malondialdehyde, more particularly malondialdehyde from blood platelets.

According to this invention, a series of samples containing malondialdehyde and segmented by gas are prepared. These samples are submitted to a dialysis to remove the proteins, and the malondialdehyde content is determined by colorimetry.

Although the invention is not limited to the determining or titrating of malondialdehyde from blood platelets, this is a preferred application.

The blood platelets are capable of producing substantial amounts of endoperoxides from arachidonic acid. This transformation is carried out owing to the enzymatic system of cyclooxygenases.

The endoperoxides change in turn into various metabolites including malondialdehyde (MDA). It is known that a single oral dose of acetylsalicylic acid (aspirin) alters irreversibly the platelet cyclooxygenase system and thus inhibits the production of endoperoxides from the blood platelets. The production of MDA, a metabolic derivative of the endoperoxides, is also irreversibly inhibited. Thus, the determining of the MDA platelet content, before and after a simple oral dose of acetylsalicylic acid leads to the possibility of evaluating platelet regeneration.

Indeed, platelets which have been "touched" in vivo by acetylsalicylic acid lose irreversibly their ability to produce normally MDA; on the other hand, this inhibition phenomenon does not take place for the platelets which circulate after the removal of aspirin which is otherwise very rapid. Consequently, if the MDA levels are compared with the levels present before the acetylsalicylic acid dose, by drawing suitable diagrams, the platelet regeneration time can be obtained.

By considering these basic data, it appears that, in opposition to the $^{51}$Cr method, this technique measures the platelet production rate from the bone marrow, rather than their removal rate.

A particular embodiment for determining malondialdehyde content according to the invention, as a nonlimiting example, is described below.

This is a semi-automatic determination of malondialdehyde from blood platelets.

It comprises a manual step for the preparation of samples containing malondialdehyde and an automatic step for the actual determination of the malondialdehyde contained in these samples. It has to be understood that this first step could also be automated in order to obtain an entirely automatic process.

MANUAL STEP 9 ml of human venous blood are collected and anticoagulated by one ml of a 0.129 M trisodium citrate solution. The platelet-enriched plasma (PRP) is obtained by centrifuging whole blood at 200 XG for 10 min. (22° C.). The platelet counting is carried out on each sample of PRP by means of a Thrombocounter (Coulter Electronics). The platelet buttons are obtained by centrifuging (2000 XG; 30 min; 21° C.) 2 ml of PRP. These buttons are suspended in 2 ml of phosphate buffer pH 7,4 ($Na_2HPO_4$, 1,36% weight/vol; NaOH 0.33% w/v) and incubated for 15 min. at 37° C. in the presence of N-ethylmaleimide (1 mM; NEM) or arachidonic acid (0,64 mM; AA). These agents stimulate the production of platelet MDA. After this incubation period, the samples are treated ultrasonically for 15 min. The platelet wastes are removed by filtration through seraclear filters.

AUTOMATIC STEP

The flow-diagram of the flows for the automatic determination of the malondialdehyde from the blood platelets is shown in the annexed Figure. The various Technicon ® modules used for this determination are as follows: a sample distributor of type II capable of taking 40 samples per hour (taking ratio: sample-rinsing: 2-1); a proportionating peristaltic pump with multitubes of type II; a dialysis unit provided with a cuprophane membrane maintained at 37° C.; a thermocontrollable oil bath, the temperature of which is set at 82° C.; a colorimeter provided with a tubular tank with a 15 mm optical path and a 530 nm filter, a pen recorder with a four-time scale expander; a voltage transformer and stabilizer.

Two solutions of perchloric acid (PCA) are prepared with a concentration of 2 and 10% (vol/vol) respectively. 0.05% of Brig-35 (vol/vol) is added to each solution to regulate the bubbling of the flow.

A 0.8% (w/vol) solution of 2-thiobarbituric acid solution is prepared according to the techniques described in Marie J. Stuart, M.B., B.S., Scott Murphy, M.D. and Frank A. Oski, M.D.: "A Simple Non-Radioisotope Technique for the Determination of Platelet Life-Span," *The New England Journal of Medicine*, June 19, 1975, pp. 1310–1313.

The 10% PCA solution is mixed with the sample flow previously segmented by air or any other gas. The precipitated proteins are removed by a dialysis at 37° C. and the MDA is taken up with a counter-dialysis bubbled flow with 2% PCA. The 2-thiobarbituric acid solution is added to the counter-dialysis flow. An incubation during 10 min. at 82° C. permits the buildup of the pink-coloured complex between the MDA and 2-thiobarbituric acid. This colouration is read at 530 nm after cooling of the mixture at room temperature by a heat exchanger (Sinned-cooler).

A 10 mM solution of MDA is prepared by hydrolysing malondialdehyde tetraethylacetal with 0.5 N hydrochloric acid. Calibration curves are drawn from MDA solutions the concentration of which varies between 0.25 and 3 nmoles/ml. These solutions are obtained by diluting the mother liquor with distilled water.

COMPATIBILITY LIMIT OF THE AUTOMATIC DETERMINATION OF THE MDA (a) the rate of the sample distributor can be varied within the range of 20 to 70 samples per hour. The sample-rinsing proportion can vary from a 2-3 ratio to a 2-1 ratio.

(b) the driving speed of the pump motor can be modified as required.

(c) the time period of the dialysis can, for example, be varied between 1 and 10 min. and is preferably of the order of 3 min., whereas the temperature is generally between 20° and 50° C. and is preferably between 35° and 40° C. However, the conditions given in the above-mentioned example are the optimalized ones. The counter-dialysis flow can be an aqueous acid solution of low strength. The kind of the acid is of relatively little importance but its strength cannot preferably exceed 5%.

Besides perchloric acid (PCA), $H_3PO_4$, $CH_3COOH$ and $CCl_3COOH$ can be used, for instance.

(d) The acid strength used to precipitate the proteins is not critical. For the PCA, for example, strengths of 5% to 12% could be used. However, the use of high PCA strengths results in corrosion problems, especially with regard to the dialysis system. In this stage of the process, the PCA could be also replaced by one of the other above-mentioned acids. The acid could be identical with or different from the acid used for the counter-dialysis.

(e) A decrease of the 2-thiobarbituric acid strength or concentration leads to a decrease of the colouration. An increase of the 2-thiobarbituric acid strength provides no increase in sensitivity.

(f) The residence time in the oil bath and the temperature thereof are critical in the above-described system. Indeed, a temperature increase prevents good control of the flow and a temperature decrease leads to a loss of sensitivity.

The described colouration time (10 min.) is sufficient to complete the reaction between the MDA and 2-thiobarbituric acid. This time can be increased but cannot be decreased.

In conclusion, the above-described conditions for the automatic determination of platelet MDA are optimalized. Any variation of the flow-diagram shown in the annexed FIGURE could lead to a loss of sensitivity. However, this loss could be obviated by an electronic amplification of the output signal of the colorimeter.

The device for working the automatic step to which reference has already been made, and which has been shown in the annexed FIGURE, is described in detail hereinafter.

This device comprises in sequence the following apparatus: a sample distributor 1, a dialyzer 2, an oil bath 3, a colorimeter 4 and a recorder 5.

The sample distributor is connected to the dialyzer 2 through a tube 6. To this tube, are connected successively an air inlet 7 to segment the sample fed through the dialyzer into substantially constant-length and equidistant portions and a 10% perchloric acid supply 8 to mix the acid with the sample in order to precipitate the proteins. Furthermore, downstream of the location where the perchloric acid is contacted with the sample, mixing coils 9 are provided on the pipe 6, to allow the production, in this location, in the tube 6, of a substantially turbulent flow insuring a homogenous mixture of the perchloric acid and the samples. The precipitated proteins are removed in 10.

A duct 11, to which is connected a further air inlet 12, provides the above-mentioned bubbled flow of counter-dialysis of 2% perchloric acid. The 2-thiobarbituric acid solution is added to the flow through a duct 13. The whole is then mixed in a further series of mixing coils 14 before being passed through the oil bath 3 where a temperature on the order of 82° C. is maintained.

The flow having passed through this bath is then fed through a pipe 15 to the colorimeter 4, after it has been cooled to room temperature in a cooler 16 of the "Sinned-cooler" type.

Part of the sample passes through the colorimeter 4 for measurement of the MDA content, the excess is previously exhausted in 18, through a duct 17. That part which has passed through the colorimeter then passes through the duct 19 and exhausted also in 18.

Finally, a washing water feed is provided through duct 20 to rinse the taking needle of the sample distributor, to segment the sample and to mix the same with the PCA. The water and the rinsing products are eliminated in 21.

The flow rate in the various ducts, tubes and fluid inlets is provided by pump 7.

For instance, in the above-described specific example, the samples are fed by tube 6 with an inner diameter of 0.051 inch, the air by a tube with an inner diameter of 0.040 inch, and the 10% PCA by a tube with an inner diameter of 0.035 inch. The 2% PCA for the counter-dialysis is fed by duct 13 with an inner diameter of 0.056 inch, whereas the air is added to this PCA stream by a duct with an inner diameter of 0.045 inch.

The thiobarbituric acid is fed by duct 13 with an inner diameter of 0.05 inch.

The inner diameter of the rinsing water duct is 0.073 inch.

It is to be noted that the inner diameters of the various tubes can be varied within certain limits. However, to allow an automatic proportioning under optimal conditions of the MDA, the ratios of the inner diameters of these various tubes which, according to the invention, permit suitable flow rates controlled by pump 7, appear to be rather severe.

Generally, all of the conduits, tubes and ducts of the device according to the invention are made from glass.

We claim:

1. A process for determining the content of malondialdehyde in a sample which comprises:
    preparing a series of samples containing malondialdehyde;
    segmenting the samples using a gas;
    adding an acid to the samples to precipitate proteins contained in the samples;
    subjecting the samples to dialysis to separate the proteins;
    taking up the malondialdehyde with a counter-dialysis bubbled flow;
    adding a 2-thiobarbituric acid solution to the counter-dialysis flow;
    incubating said flow containing the 2-thiobarbituric acid solution for about 10 minutes at about 82° C. so as to build up a pink-coloured complex between the malondialdehyde and the 2-thiobarbituric acid; and
    determining the malondialdehyde content by colorimetry.

2. The process as defined in claim 1, wherein the acid added to the samples to precipitate the proteins is perchloric acid.

3. The process as defined in claim 1, wherein the counter-dialysis bubbled flow contains an acid having a concentration not exceeding 5% by weight and said acid is selected from the group consisting of perchloric acid, phosphoric acid, acetic acid and trichloroacetic acid.

4. The process as defined in claim 1, wherein said malondialdehyde is from blood platelets and the determining of the content of said malondialdehyde comprises:
    preparing a platelet-enriched plasma from a determined amount of blood;
    counting the platelets contained in the plasma;
    sedimenting the platelets;
    suspending the platelets at pH 7.4 by addition of a phosphate buffer;
    adding a platelet-aggregation agent which stimulates the production of platelet malondialdehyde;

segmenting the samples using said gas;

subjecting said samples to said dialysis; and adding the colorimetric reagent to said samples to determine the malondialdehyde content by colorimetry.

5. The process as defined in claim 4, wherein said platelet-aggregation agent is arachidonic acid or N-ethylmaleimide.

* * * * *